United States Patent [19]

Moy

[11] 4,266,070
[45] May 5, 1981

[54] CATALYTIC PROCESS FOR THE MANUFACTURE OF URETHANES

[75] Inventor: David Moy, Ridgewood, N.J.

[73] Assignee: Halcon Research and Development Corp., New York, N.Y.

[21] Appl. No.: 42,676

[22] Filed: May 25, 1979

[51] Int. Cl.³ .................. C07C 125/063; C07C 125/07
[52] U.S. Cl. ........................................ 560/24; 260/464;
260/465 D; 260/465.4; 560/9; 560/25; 560/26;
560/27; 560/29; 560/30; 560/31; 560/32;
560/33; 560/115; 560/132; 560/133; 560/135;
560/136; 560/137; 560/148; 560/157; 560/158;
560/159; 560/160; 560/161; 560/162; 560/163;
560/164; 560/165; 252/438; 525/439; 252/440;
252/441; 252/472
[58] Field of Search ............... 260/465 D, 464, 465.4;
560/9, 24, 25, 26, 27, 29, 30, 31, 32, 33, 115,
132, 133, 135, 136, 137, 148, 157, 158, 159, 160,
161, 162, 163, 164, 165

[56] References Cited

U.S. PATENT DOCUMENTS

| | | | |
|---|---|---|---|
| 3,099,689 | 7/1963 | Cragg | 560/561 |
| 3,338,956 | 8/1967 | Morentfield | 560/24 |
| 3,384,655 | 5/1968 | Anderson et al. | 560/24 |
| 3,448,140 | 6/1969 | Gamlen et al. | 560/24 |
| 3,454,620 | 7/1969 | Gamlen et al. | 560/24 |
| 3,467,694 | 9/1969 | Hardy et al. | 560/25 |
| 3,531,512 | 9/1970 | Hardy et al. | 560/25 |
| 3,629,311 | 12/1971 | Anderson et al. | 260/455 B |
| 3,895,054 | 7/1975 | Zajacek et al. | 560/25 |
| 3,956,360 | 5/1976 | Zajacek et al. | 560/24 |
| 3,993,685 | 11/1976 | Zajacek et al. | 560/24 |
| 3,993,685 | 11/1976 | Zajacek et al. | 560/24 |
| 4,052,437 | 10/1977 | Licke | 560/24 |
| 4,080,365 | 3/1978 | Hirai et al. | 560/24 |
| 4,100,351 | 7/1978 | Romono et al. | 560/25 |
| 4,134,880 | 1/1969 | Miyata et al. | 560/24 |
| 4,170,708 | 10/1979 | Hirai et al. | 560/24 |
| 4,178,455 | 12/1979 | Hirai et al. | 560/24 |
| 4,186,269 | 1/1980 | Hirai et al. | 560/25 |

FOREIGN PATENT DOCUMENTS

| | | |
|---|---|---|
| 634690 | 1/1962 | Canada. |
| 815 | 2/1979 | European Pat. Off. . |
| 1486399 | 9/1977 | United Kingdom. |

OTHER PUBLICATIONS

Balling, et al., "Chem. Absts." 73, 66302 (p) 1970.
Franz et al., J. Org. Chem., 26, 3309 (1961).
Baiocchi, et al., J. Org. Chem., 21, 1546, 1956.

Primary Examiner—Natalie Trousof
Assistant Examiner—G. T. Breitenstein
Attorney, Agent, or Firm—William C. Long; David Dick; Jack B. Murray, Jr.

[57] ABSTRACT

A process for the production of urethanes is provided in which an organic primary or secondary amine is contacted, in the substantial absence of reactive oxygen, with a source of carbon monoxide and an organic compound containing at least one hydroxyl group in the presence of a catalyst comprising a member selected from the group consisting of carbonyls of Co, Mo, Ti, Rh, Fe, Ni and mixtures thereof. Urethane yields and selectivities are further improved by conducting the reaction in the additional presence of an organic compound containing at least one C≡N or C≡C group. When such unsaturated organic compounds are employed, the catalyst can additionally comprise iridium carbonyl.

15 Claims, No Drawings

CATALYTIC PROCESS FOR THE MANUFACTURE OF URETHANES

CROSS-REFERENCE TO RELATED APPLICATION

This application is related to my co-pending applications, Ser. No. 7,104, filed Jan. 29, 1979, and Ser. No. 7,105, filed Jan. 29, 1979, and is also related to the application of R. Harvey, Ser. No. 42,675, filed May 9, 1979, filed on even date herewith.

BACKGROUND OF THE INVENTION

1. FIELD OF THE INVENTION

This invention relates to the preparation of urethanes and more specifically to the preparation of urethanes by the direct carbonylation of primary and secondary amines.

2. DESCRIPTION OF THE PRIOR ART

Urethanes, which are also referred to herein as "carbamates" are industrial chemicals of enormous significance, and much research has been performed in search of economical process for their manufacture. One such process involves the formation of a primary amine such as aniline from the corresponding organic nitro compound (e.g., nitrobenzene) and reaction of the resulting primary amine with phosgene to form a carbamyl chloride salt which is then thermally decomposed to corresponding isocyanate. Recovery and reaction of the isocyanate with an alcohol yields the urethane. Due to the high toxicity of phosgene, and to the corrosive nature of systems in which the chloride ion is employed, alternative processes have been sought which would remove these disadvantages.

U.S. Pat. No. 3,467,687 relates to the preparation of organic isocyanates by reacting an aromatic nitroso compound with CO in the presence of catalyst and a Lewis acid under anhydrous, hydrogen-free conditions. U.S. Pat. No. 3,641,092 reacts a primary amine with CO and palladium chloride to form isocyanates. U.S. Pat. No. 3,405,156 forms isocyanates from saturated aliphatic primary amines or aromatically unsaturated primary amines by reaction of the amine with CO and a platinum group metal salt. See also E. W. Stern, et al., 31 *J. Org. Chem.* 596 (1965). U.S. Pat. No. 3,070,618 relates to the production of polyisocyanates from polyamines and CO by reaction with a metal carbonyl (or suitable mixtures of CO and oxygen) under catalytic conditions.

U.S. Pat. No. 3,644,462 produced isocyanates by carbonylation or organic nitro compounds employing a catalyst system comprised of a noble metal halide and certain primary, secondary and tertiary amines. However, the selectivity to the isocyanate was comparatively low and the required recovery and conversion of the isocyanate to a urethane product would be expected to reduce selectivities to the urethane still further.

Accordingly, a large number of processes were developed to carbonylate an organic nitro compound with carbon monoxide in the presence of an organic hydroxy compound and certain catalyst systems to obtain the corresponding urethane. Exemplary references to these processes and their catalyst systems are as follows: (1) U.S. Pat. No. 3,338,956 (carbonyls of metals of Groups VI-B, VII-B and VIII); U.S. Pat. No. 3,448,140 (complex compound of a transition metal having atomic number of 21 to 29, 39 to 47 and 71 to 79, inclusive, containing ligands of P, As, or Sb); U.S. Pat. No. 3,467,694 (noble metal and a Lewis acid); U.S. Pat. No. 3,531,512 (palladium and a Lewis acid; U.S. Pat. No. 3,895,054 (Se, S or Te); U.S. Pat. No. 3,956,360 (Se, S or Te); U.S. Pat. No. 3,993,685 (tertiary amine and a platinum group metal or compound thereof); U.S. Pat. No. 4,052,437 (rhodium oxide); and U.S. Pat. No. 4,080,365 (Se+base+aromatic amino or urea promoter); (2) British Pat. No. 1,089,132 (metal carbonyls of Groups VI-B, VII-B and VIII and multivalent metals or their salts); British Pat. No. 1,469,222 (palladium group metal halide and a nitrogen-containing heterocyclic compound); and 1,485,108 (Se); and (3) French Patent of Addition No. 2,008,365, as cited in 73 *Chem. Abs.* 66 302p (1970) (palladium, $Al_2O_3$ or $Fe_2O_3$).

Urethanes have also been formed by reacting an alcohol with urea. See, e.g., P. Adams, et al., *Chem. Rev.*, vol. 65, 567, 569–572 (1965).

While the above processes allow direct formation of urethanes from nitro- and urea-compounds, a one-step process for converting amines to urethanes would also be advantageous.

However, it was long believed that carbonylation of aromatic amines only yields ureas or formamides. Thus, Hagelloch, *Ber.*, vol. 83, 258 (1950) reacted aniline and COS in ethanol to form low yields (1–3%) of 1,3-diphenyl urea, and German Pat. No. 863,800 (1953) converted aniline to high yields of urea and/or N-substituted formamides with CO in the presence of nickel iodide, powdered nickel or cobalt (activated with MgO or $SiO_2$) as catalyst. See also H. W. Steinberg, et al., 75 *J. Amer. Chem. Soc.*, 3148 (1963) (reaction of dimethyl amine with $Co_2(CO)_8$ to form tetramethyl urea), and G. Natta, et al., 74 *J. Amer. Chem. Soc.*, 4496 (1952) (synthesis of amides by cobalt catalyzed reaction of amine, CO and olefin; e.g., reaction of styrene, aniline and CO to form a mixture of diphenyl urea, betaphenylpropionamide and ethyl benzene).

U.S. Pat. No. 4,052,452 formed unsymmetrical ureas by the reaction of nitrogeneous organic compounds with aniline, carbon monoxide and sulfur or selenium and certain bases, and British Pat. No. 1,275,702 produced ureas from primary or secondary mono- or diamines by reaction with CO in the presence of Se. N. Sonoda et al., *J. Amer. Chem. Soc.*, vol. 92 (23), p. 6344 (1971) obtained very high yields of urea from ammonia or aliphatic amines, CO and $O_2$ in the presence of Se, and K. Kondo et al., *J. Chem. Soc. Chem. Comm.*, 307 (1972) obtained stoichiometric yields of ureas by carbonylation of aromatic amines with CO, $O_2$ and Se, employing a strongly basic tertiary amine, such as triethyl amine, as co-catalyst.

R. A. Franz et al., 26 *J. Org. Chem.* 3309 (1961) found that tertiary aliphatic amines, KOH and CaO or MgO in methanol were urea catalysts in the reaction of aromatic amines with CO and S. U.S. Pat. No. 2,877,268 disclosed obtention of "excellent yields" of urea by use of alkaline catalysts with a dissociation constant of greater than $1 \times 10^{-10}$: tertiary alkyl amines of 1 to 18 carbon atoms, quaternary ammonium hydroxides, alkaline earth metal and alkali metal hydroxides, alkaline and alkali metal salts (such as sodium oleate), MgO (in methanol), Ca (in methanol) and certain substituted aryl and aralkyl amines. Similarly, diuredides were obtained in Canadian Pat. No. 634,690 by reacting aromatic diamines with CO,S and certain aliphatic or aromatic secondary amines in methanol.

Thio-derivatives of amines have also been produced by carbonylations. U.S. Pat. No. 3,636,104 formed N,N'-diaryl thioureas by reacting aniline, with $CS_2$ in pyridine or alcohol with the addition of S or $H_2O$. Alkylamine salts of N-alkyl thiocarbamic acid were prepared in U.S. Pat. No. 2,655,534 by reacting COS and a primary or secondary aliphatic amine. U.S. Pat. Nos. 3,392,197 and 3,539,587 prepared substituted thioureas and monothiocarbamates from primary and secondary amines employing CO and sulfur or sulfur compounds. Thiocarbamates have also been prepared by reaction of amines and disulfides in equimolecular ratio with carbon monoxide in the presence of selenium catalysts and triethylamine. See P. Koch, *Tetrahedron Letters* No. 25, pp. 2087–2088 (1975); West German Patent Publication No. 2,617,917, as cited in 86 *Chem. Abs.* 43426 m (1977).

In attempting to carbonylate amines to a urethane product, F. Baiocchi, et al., 21 *J. Org. Chem.* 1546 (1956) prepared methyl-N-phenyl urethane in low yield (27–30%, based on aniline charged) by reacting aniline and COS in methanol employing either zinc peroxide, di-tert-butyl peroxide or $O_2$ to induce the reaction. Magnesium peroxide was found to be not operative, and other peroxides ($H_2O_2$ in $H_2O$ and cumene hydroperoxide in methanol, with and without sodium methoxide), yielded very large amounts of 1, 3-diphenyl urea. Netherlands Pat. No. 94,613 converted aliphatic primary and secondary amines to urethanes by reaction with CO in the presence of alcohols and stoichiometric amounts of certain cupric compounds, which were reduced to the cuprous state, and required reoxidation, as by $O_2$, to regenerate the cupric reactant.

R. A. Franz et al., 28 *J. Org. Chem.* 585 (1963) also obtained urethanes from aniline, COS and methanol in the presence of triethyl amine, but could not achieve urethane yields greater than about 13.5%. Even using a carefully controlled, multi-step process, urethane yields greater than 25% were not obtained by Franz et al. under any combination of experimental conditions. Stoichiometric reaction of certain metal acetates ($Hg^{+2}$, $Tl^{+3}$ and $Cu^{+2}$) in T. Saegusa, et al., *Tetrahedron Letters* No. 42, pp. 4123–4126 (1967) with piperidine, CO and $CH_3OH$ did not greatly improve urethane yields. Use of the metal acetates of $Ag^{+1}$, $Cd^{+2}$ and $Zn^{+2}$ gave only trace carbamate product, even after 98 hours of reaction.

Higher urethane yields have been provided by U.S. Pat. Nos. 3,384,655 (issued in 1968 to Anderson et al.) and 3,629,311 (issued in 1971 to Anderson et al.) and K. Kondo, et al., *Chem. Letters*, pp. 373–374 (Chem. Soc. Japan 1972). In the Anderson et al. process, a secondary (or a mixture of secondary and teritary) amine is first reacted with COS and an alcohol to form an adduct containing the urea, COS and alcohol, followed by a low temperature oxidation of the adduct with $O_2$, optionally in the presence of soluble Fe, Ni, Co, Cu, Hg, Pd, Pt or Au halide, sulfate or nitrate promoters, to form the desired urethane, elemental sulfur and water. Kondo et al. reacted a primary amine, CO, Se and methanol in the presence of triethylamine, followed by oxidation with $O_2$ of the foregoing mixtures, to yield the urethane, and to form a Se precipitate and water. However, the required use of $O_2$ (or peroxides as in the Baiocchi process) is industrially severely disadvantageous due to the ease with which aniline is oxidized to a wide variety of by-products and due to the obvious explosive hazards associated with mixtures of oxygen, carbon monoxide and alcohol. The explosive hazards require careful attention to temperature controls and use of expensive processing equipment. A further disadvantage to the use of oxygen is the by-product water which is formed and which then reacts with the carbamate to ultimately form a urea. To avoid the urea problem, water absorbing agents must be added and additional care must be taken to use anhydrous reactants to avoid further urea being formed. Both of these precautions require added processing expense.

U.S. Pat. Nos. 3,445,497, 3,502,706 and 3,632,624 relate to the formation of an adduct by reaction of tertiary amines, alcohols and carbon dioxide in the presence of certain metallic salts. These adducts are then further reacted to form such products as metal alkyl carbonates and thiolcarbonates.

European Patent Publication No. 815 (Mitsui Toatsu Chemicals, published Feb. 21, 1979) (which is not believed by applicant to comprise prior art) relates to the preparation of N-aryl or N-aralkyl substituted urethanes from aryl or aralkyl primary amino compounds substituted with a nitro, nitroso or carbamate group, by reaction with an organic hydroxyl-group containing compound and CO in the presence of a catalyst comprising a Pd, Rh or Ru metal compound and a Lewis acid compound promoter, preferably in the presence of from 1 to 70 moles of water per mole of the aryl or aralkyl primary amino compound. However, this process is not readily adaptable to producing carbamates using other catalyst systems, and the Mitsui Toatsu applicants were unable to obtain detectable carbamate employing aryl or aralkyl primary amines which were not so substituted.

R. Harvey, in application Ser. No. 42,675 cited above, discloses a process for preparing urethanes in which a primary or secondary amine is contacted in the substantial absence of reactive oxygen with a source of CO, an organic compound containing at least one hydroxyl group and a metal reactant. The metal reactants employed are compounds and complexes of Group VIII of the Periodic Table. While urethanes are obtained in significant quantities, the process is subject to further improvement in terms of yields of, and selectivity to, the urethane products.

SUMMARY OF THE INVENTION

It has been surprisingly found that urethanes can be prepared in good yields according to the improved process of the present invention, by which an organic primary or secondary amine is contacted, in the substantial absence of reactive oxygen, with a source of carbon monoxide and an organic compound containing at least one hydroxyl group in the presence of a catalytically effective amount of a catalyst selected from the group consisting of Co, Mo, Ni, Fe, Rh and Ti carbonyls, and mixtures thereof.

It has been found that the cobalt carbonyl catalyst system of this invention is surprisingly, unexpectedly superior to other metals including V, Mn, Re, Pd and Pt. Moreover, the present invention provides outstanding unexpectedly improved carbamate yields, even over those obtained using non-carbonyl forms of cobalt.

It has been further discovered that even greater yields of urethane can be obtained if the reaction is conducted in the presence of an unsaturated organic compound containing at least one C=N or C=C group. The use of such unsaturated compounds has also been found to permit use of iridium carbonyl as a catalyst for the reaction.

These advantages are achieved using very low concentrations of the above catalysts, thereby avoiding the requirement of prior art processes in which stiochiometric levels of metal reactants were used. Importantly, the present invention removes the requirement of using molecular $O_2$ or a peroxidic reactant to effect the formation of the urethane product, minimizing the safety hazards and urea-formation problems attending the use of such reactants. Further, the amine reactants of this invention are not required to be first substituted by a $NO_2$, $NO$ or carbamate group as in European Patent Application 815, cited above.

DETAILED DESCRIPTION OF THE INVENTION

Any organic primary or secondary amine capable of being converted to an organic urethane may be employed as a reactant. Aliphatic amines, alicyclic amines and aromatic amines are operable. These amines include primary amines of the formula $RNH_2$ wherein R is alkyl, aryl, alkaryl, aralkyl, and cycloalkyl, and secondary amines of the formula $RNH(R')$ wherein R and R' are independently selected from the group consisting of alkyl, aryl, alkaryl, aralkyl and cycloalkyl. Also included as operable organic amines are primary and secondary amines containing fused rings and heterocyclic substituents. The primary and secondary amines may be substituted or unsubstituted, and when substituted preferably contain inert substituents such as alkyl, aryl, alkaryl, aralkyl, cycloalkyl, halogen (Cl, Br, F and I), alkylcyano, tertiary amino, esters, ethers and thioether groups. Preferably, the amine reactant contains no substitution by $OH—$, $>C=O$ (i.e., ketonic or aldehydic) or sulfonic acid groups since such groups interfere with the desired carbonylation reaction to the selected carbamates. The foregoing suitable hydrocarbon substituents to the R and R' groups can themselves be substituted by one or more amino groups. Exemplary of such amino substituted hydrocarbyl substituents to the R and R' groups are amino-substituted aralkyls (e.g.,

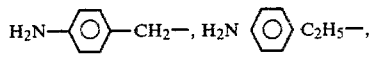

and the like), amino-substituted alkyl (e.g., $H_2NCH(CH_3)—$, $H_2NC_2H_5—$ and the like) and amino-substituted alkaryls (e.g.,

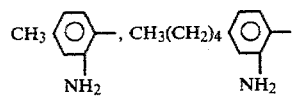

and the like).

Also included as reactants in this invention are amines of the formula $R(NH_2)_m$ wherein R is as defined above and wherein m is an integer of from 2 to 5, preferably of from 2 to 3. Thus, aliphatic, alicyclic and aromatic diamines, such as ethylenediamine, hexamethylenediamine and other homologues and isomers of 2 to 10 carbon atoms are operable. The aromatic diamines include phenylenediamine, toluenediamine and naphthylenediamine. Phenylenetriamine also is operable. Polymeric amines having repeating polymer units based on any of the above amines can also be used (e.g., polymeric methylene dianiline).

Examples of R and R' substituents of the amines of each of the above formulas are alkyl radicals derived from straight and branched-chained alkanes of from 1 to 20, preferably from 1 to 12, carbon atoms (such as methyl, ethyl, isopropyl, butyl, decyl, dodecyl, isostearyl, and the like); aryl of 6 to 18, preferably 6 to 12, carbon atoms (such as phenyl, naphthyl, anthryl and the like), alkaryl and aralkyl of 7 to 24, preferably 7 to 12, carbon atoms (such as benzyl, tolyl, p-butyl phenyl, dihexylphenyl; isostearyl phenyl, and the like) and cycloalkyl of 3 to 12 carbon atoms (such as cyclohexyl, cyclopentyl, cyclobutyl, cyclododecyl and the like).

Typical examples of suitable amines which can be reacted to form carbamates include the following primary amines such as aniline, tolyl amines, xylyl amines, naphthyl amines, anthryl amines, benzyl amine, 1- or 2-bromoethyl benzyl amine, cyclohexylamine, bis-aminoaryl-substituted alkylenes (e.g., compounds of the formula

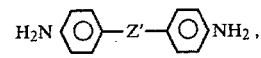

wherein Z is alkylene of 1 to 6 carbon atoms, such as methylene, ethylene, trimethylene, tetramethylene and the like), the diamino toluenes and the like.

Especially preferred as amines in the process of this invention are primary amines of up to 14 carbon atoms. Most preferred are aromatic primary mono- and diamines of from 6 to 13 carbon atoms. Examples of most preferred monoamines are aniline, and of most preferred diamines are 2,4-diamino-toluene and 4,4'-methylene dianiline.

The source of the carbon monoxide employed as reactant in this invention is not critical and thus carbon monoxide can be employed, in any form (e.g., as a gas), as a pure material, or in admixtures with other materials which do not adversely affect the desired reaction. For example, carbon monoxide gas can be employed in admixture with materials normally found in synthesis gas (generally containing from about 50 to 80 volume % CO), such as hydrogen, $CO_2$ and the like. Of course, inert gases such as $N_2$, Ar and the like can be present. The carbon monoxide can also be introduced to the reaction zone in a chemically combined form with one or more of the desired components of the catalyst system. For example, the carbon monoxide can be chemically combined as a metal carbonyl, which under the conditions of the reaction will release carbon monoxide for reaction in the process with the desired amine. Such metal carbonyls are known materials and include Co, Mn and Fe carbonyls. Thus, as used herein, the term "source of carbon monoxide" is intended to refer to CO or a chemically combined or complexed form thereof which releases CO under the conditions of the reaction. The preferred source of carbon monoxide is CO.

The reaction is preferably conducted in the substantial absence of "reactive oxygen", that is, the amount of molecular oxygen, and organic and inorganic peroxides in the reaction zone, whether dissolved, suspended, or in the gaseous state, should be less than 1 weight percent, and preferably less than about 0.1 weight percent, of amine reactant charged to the reaction zone.

Organic compounds containing at least one hydroxyl group suitable for use in the process in the present invention include mono- or polyhydric alcohols containing primary, secondary or tertiary hydroxyl groups and mixtures thereof. The alcohols can be aliphatic or aromatic and can bear other substituents in addition to hydroxyl groups, but the substituents should, except as hereinafter defined, preferably be non-reactive with carbon monoxide under the process conditions.

Generally, the hydroxyl group-containing compounds comprise compounds of the formula $Z(OH)_n$ wherein n is 1 or more and preferably from 1 to 3, and Z is an optionally substituted aryl, aliphatic, cycloaliphatic or araliphatic group, preferably containing from 1 to 20 carbon atoms, more preferably from 1 to 7 carbon atoms. The group Z can therefore be alkyl, cycloalkyl, alkylene, cycloalkylene, aryl, or aralkyl, which groups can be substituted by alkyl, alkoxy, aryl or aryloxy groups normally containing up to 7 carbon atoms, and derivatives of the foregoing in which one or more carbon atoms are substituted by oxygen, nitrogen or sulfur atoms. The foregoing groups can also be substituted by sulfoxide, sulfone, tertiary amine, amide or carboxylic ester groups.

Exemplary hydoxyl group-containing compounds are monohydric alcohols such as methanol, ethanol, n-propanol, sec-propanol, n-, iso- and tert-butanol, amyl alcohol, hexyl alcohol, lauryl alochol, cetyl alcohol, benzyl alcohol, chlorobenzyl alcohol, methoxy benzyl alcohol, methoxy ethanol, butoxy ethanol, cyclohexyl alcohol, phenol and the like. Exemplary polyhydric compounds include diols such as ethylene glycol, diethylene glycol, propylene glycol and dipropylene glycol, triols such as glycerol, trimethylolpropane, hexanetriol, tetrols such as pentaerythritol and the like. Ethers of the foregoing polyols can also be employed provided that at least one OH group remains unetherified. The etherifying group in such ether alcohols normally will contain up to 4 carbon atoms and are preferably selected from the group consisting of alkyl, cycloalkyl or aralkyl groups which can themselves be substituted.

Especially suitable hydroxy-containing compounds are the lower mono- and polyhydric alkanols. Exemplary of such especially suitable compounds are methanol, ethanol, n-propanol, isopropanol, butanol, sec-butanol, isobutanol, ethylene glycol, glycerol and trimethylol propane.

The catalysts employed in the broad practice of this invention comprise at least one member selected from the group consisting of carbonyls of cobalt, molybdenum, nickel, iron and titanium. Additionally, iridium carbonyl can be employed as the catalyst if the reaction is conducted in the presence of an unsaturated compound, as will be more fully explained below. It will be understood that the carbonyl catalysts of this invention are known materials and comprise chemical complexes of the metal (e.g., Co, Mo, Fe, Ti, Ni, Rh or Ir), primarily in the zero valence state, and CO moieties. The number of CO groups associated with each metal molecule in such carbonyls is not critical. Thus, typical carbonyls include dicobalt octacarbonyl, tetracobalt dodecacarbonyl, molybdenum hexacarbonyl, di-iron nonacarbonyl, iron pentacarbonyl, iron tetracarbonyl, nickel tetracarbonyl, di-iridium octacarbonyl, tetrairidium dodecacarbonyl, titanium carbonyl complexes, rhodium carbonyl, and the like. Preferred catalysts of this invention are cobalt carbonyl, molybdenum carbonyl and titanium carbonyl, with cobalt carbonyl being especially preferred. The metal carbonyl catalyst can contain, either as a physical or chemical admixture, combination or complex with the catalytically active metal carbonyls of this invention, a wide variety of other materials such as, for example, any of the halides (Cl, F, I or Br). Preferably, the catalyst is substantially free of triaryl phosphine (e.g., triphenyl phosphine) since it has been found that such materials can decrease product yields which would otherwise be obtained.

A wide variety of organic solvents can also be employed in the reaction zone. Suitable organic solvents include alkanes such as cyclohexane, hexane, octane and the like; aromatic solvents such as benzene, toluene, xylene; nitrile solvents such as acetonitrile and benzonitrile; amide type solvents such as N, N-dimethyl formamide and N, N-dimethyl acetamide; aliphatic, alicyclic or aromatic sulfoxide and sulfone solvents, such as dimethyl sulfoxide; aliphatic halogenated hydrocarbons such as 1, 1,2-trichloro-1, 2, 2-trifluoroethane; halogenated aromatic hydrocarbons such as monochlorobenzene, dichlorobenzene and trichlorobenzene; esters; and ether solvents such as tetrahydrofuran, 1,4-dioxane, 1,2-dimethoxyethane and the like. The ether compounds, for example, can be aliphatic, aromatic or heterocyclic, and they can also be either mono or polyethers, or combinations of these compounds. When the hydroxy-containing organic compound is a liquid under reaction conditions, it sometimes can function as a solvent and is generally preferred.

At higher temperatures and pressures the process of the invention can advantageously be carried out in an inert diluent. The preferred inert diluents are those in which the non-gaseous reactants are soluble, including some of the solvents mentioned above. Suitable inert diluents include aliphatic or aromatic hydrocarbons such as n-pentane or toluene, ethers and esters.

Water is detrimental to urethane yields employing the process of this invention, and, therefore, it is preferred to employ substantially anhydrous reaction conditions and to employ as reactants those that are substantially anhydrous, although minor amounts of water introduced, for example, as water of hydration in the carbonyl catalyst, can be introduced without marked effect on product yield or quality. In general, the amount of water in the reaction zone should be limited to a concentration of less than about 1 weight percent, based on the amine reactant charged to the reaction zone. To effect such desired low levels of water, a water absorbing agent can also be employed in the reaction zone. Suitable water absorbing agents are described in U.S. Pat. Nos. 3,384,655 and 3,629,311. The need for such water absorbing agents is further reduced by the fact that water is not a by-product of the reaction to the desired urethane using the process of this invention. As used herein, the term "in the substantial absence of water" is intended to refer to water concentrations of less than about 1 weight percent, based on the amine reactant charged to the reaction zone.

Further improved urethane yields are obtained when there is employed in the reaction zone of this invention at least one unsaturated organic compound having at least 4 carbon atoms per molecule and containing one or more non-aryl C=C or C=N bonds per molecule, with the proviso that each terminal non-aryl >C=CH$_2$ group which is not aryl-substituted in said organic compound must contain hydrocarbyl di-substitution on the β-carbon atom of each such terminal >C=CH$_2$ group, and with the further proviso that ring carbon atoms in any quinone-moiety in said organic compound are hydrocarbyl substituted. These unsaturated organic compounds greatly improve the yield and selectivity of the desired urethane over those values which result in the absence of such compounds, and they surprisingly permit the reaction to the urethane to be catalytic in the metal carbonyl, removing the need for back-oxidation of a metal stoichometric reactant in a separate step. While I do not wish to be limited by any theory of operation, it is my belief that these organic compounds function as hydrogen acceptors in the reaction and are converted to a hydrogenated form of the organic compound in situ. Exemplary of organic compounds which are suitable for use as hydrogen acceptors in this invention include aralkenes, e.g., having from 8 to 20 carbon atoms, and preferably from 8 to 12 carbon atoms, preferably from 3 to 7 carbon atoms; alkyl esters of unsaturated carboxylic acids having a total of from 4 to 20 carbon atoms, preferably from 4 to 12 carbon atoms, per molecule; cycloaliphatic dienes of from 4 to 12 carbon atoms, preferably from 4 to 8 carbon atoms; polynuclear aromatic compounds containing two or more aromatic rings, such as naphthalene, anthraquinone and the like; indole; alkenes having the formula (I):

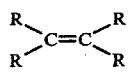
(I)

wherein the R groups are the same or different and are H or hydrocarbyl of from 1 to 10 carbon atoms, with the proviso that at least two R groups are hydrocarbyl; quinones of the formula (II):

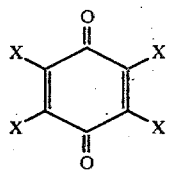
(II)

and of the formula (III):

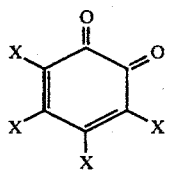
(III)

wherein the X groups are the same or different and are hydrocarbyl of from 1 to 10 carbon atoms; napthaquinones of the formula (IV):

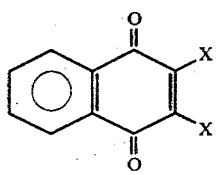
(IV)

and of the formula (V):

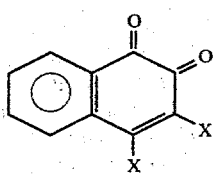
(V)

and of the formula (VI):

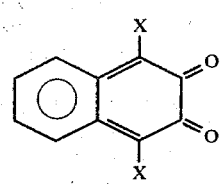
(VI)

wherein the X groups are of the same or different and are as defined above; Shiff bases of the formula (VII), (VIII) or (IX)

$X_2C=NX$ (VII)

$X-N=C-X-C=N-X$ (VIII)

$X-C=N-X-N=C-X$ (IX)

wherein the X groups are the same or different and are as defined above; aliphatic dienes of 4 to 20 carbon atoms, preferably of 4 to 8 carbon atoms, wherein any terminal $>C=CH_2$ groups are $\beta$-hydrocarbyl substituted; derivatives of the foregoing in which one or more ring carbon atom in non-quinonyl aryl groups is replaced by an oxygen, sulfur or nitrogen atom; and derivatives of the foregoing in which non-quinonyl aryl groups are substituted by one or more members selected from the group consisting of hydrocarbyl group of from 1 to 10 carbon atoms, halo (Cl, F, Br or I) and halo-substituted hydrocarbyl of 1 to 10 carbon atoms. The unsaturated compounds of this invention are preferably not substituted by $-OH$, $-NH_2$ or $-CN$ groups to avoid competing side reactions which can interfere with the formation of the desired urethane. The term "hydrocarbyl" as used herein is intended to refer to members selected from the group consisting of alkyl, aryl, aryl, alkoxy, cycloalkyl, cycloalkoxy, aryloxy, heterocyclic and carboxy. The term "quinone moiety", of course, refers to any of the 6-membered ring, cycloaliphatic diene moieties derived from para-benzoquinone or ortho-quinone. The term "non-quinonyl aryl group" therefore obviously refers to any groups which do not comprise a quinone moiety. Finally, the term "unsaturated" as used herein is intended to refer to $C=N$ as well as $C=C$ unsaturation.

As defined above, the unsaturated compounds of this invention should not contain terminal "non-aryl $>C=CH_2$ groups" (i.e., $>C=CH_2$ groups which are not part of an aromatic ring) unless these groups are either aryl-substituted, e.g., by a phenyl-group (such as is the case in styrene), or are hydrocarbyl di-substituted on the $\beta$-carbon atom. The latter requirement excludes unsubstituted linear alpha-olefins, such as hexane-1, pentene-1 and the like, which have been found unsuitable for use in this invention.

Exemplary of the foregoing $C=C$ and $C=N$ organic compounds are isobutylene, 2-methyl-1-butene, 2-methyl-2-butene, styrene, 4-(ortho-tolyl)-pentene-2, cyclopentene, 1,3-cyclopentadiene, cyclohexene, 1,3-cyclohexadiene, 1,4-cyclohexadiene, 1,4-pentadiene, 1-methyl-5-phenyl-1,5-hexadiene, 2,3-dimethyl-1,3-butadiene, 2,3-dimethyl-1,2-butadiene, 4-ethoxy-2-hexene, 1,4-ditolyl-butene-2, styrene, alpha-methyl styrene, stilbene, anthraquinone, alkyl-substituted anthraquinones (such as 2-ethyl- and 2-butyl-anthraquinones), methyl methacralate, the butyl ester of 2-hexenoic acid, dimethyl indole, naphthalene, 2,6-dimethyl-3,5-diethylorthoquinone, tetramethyl-para-benzoquinone, 2,3-dipropyl benzofuran, 2-methyl-3-isopropyl-alpha benzopyrone, 1-bromo-anthraquinone, 2-bromo-4-methyl-anthraquinone, 1,2-benz-9,10-anthraquinone, and the like.

Preferred organic compounds having such C=C or C=N groups are the aralkenes, alkyl-substituted aralkenes, stilbenes, and alkyl-substituted quinones. Exemplary of the preferred organic compounds are styrene, alpha-methyl styrene, stilbene, tert-butyl anthraquinone, ethyl-anthraquinone, tetramethyl- and tetraethyl para-benzoquinone, and the like.

The reaction is preferably carried out with at least equal molar amounts of the hydroxyl-containing compound, carbon monoxide, amine reactant and hydrogen acceptor compound (when employed) being present. Preferably, however, a molar excess of the hydroxy-containing compound is present.

The metal carbonyl catalysts of this invention will be generally used in an amount (calculated as the metal) of at least about 0.001, typically from 0.001 to 10, preferably from 0.01 to 8, and more preferably from about 0.1 to 2, weight percent of the amine reactant charged. While the catalyst can be used in larger concentrations, use of greater than about 10 weight percent will generally be uneconomical. Likewise, while less than 0.001 weight percent can be used, the reaction rate may be uneconomically low. As indicated above, when any of the foregoing hydrogen acceptor compounds are employed in the reaction zone of this invention, the catalyst can additionally comprise iridium carbonyl, so that the choice of catalysts for the reaction employing such hydrogen acceptor compounds is broadened to comprise members selected from the group consisting of carbonyls of titanium, cobalt, molybdenum, iron, nickel and iridium.

The monohydric hydroxyl-containing organic compounds will generally be used in at least an equimolar amount with the amine reactant, with the mole ratio of monohydric hydroxyl-compound to amine reactant preferably being from at least 2:1 to about 20:1, and most preferably from about 6:1 to 12:1. The amount of polyhydric alcohol which will generally be employed as the hydroxyl-containing organic compound can be determined from the foregoing mole ratios of monohydric alcohol to amine reactant and will, of course, be based on the number of reactive hydroxyl groups in each molecule of the alcohol, e.g., at least 0.5 mole of ethylene glycol will generally be used for each mole of amine reactant in the preparation of the corresponding N-phenyl carbamate derivative of ethylene glycol.

The hydrogen acceptor compounds containing one C=C or C=N group per molecule, when present, will generally also be used in at least an equimolar amount with the amine reactant, with the mole ratio of the hydrogen acceptor to amine reactant being preferably from at least 1:1 to about 4:1, more preferably from at least 1:1 to 2:1. The amount of the hydrogen acceptor compounds containing two or more C=C or C=N group per molecule can be determined in the foregoing mole ratios and will, of course, be based on the number of reactive C=C or C=N groups in each molecule of the organic compound.

In calculation of the amount of the reactants and catalysts, the term "amine reactant" is intended to refer to the active nitrogen containing group, e.g., the amine group, in the reactant. Thus, if the amine reactant is a diamino compound, for example, ethylenediamine, the number of moles of the amine reactant in the above molar ratios would be one half, i.e., the equivalent ratio.

The amount of solvent is also not critical and, where used, will generally range from about 1 to 50 weight percent, and preferably from about 10 to 40 weight percent, of the reaction mixture.

The order of mixing the reactants is not critical and can be varied within the limitations of the equipment employed. A simple procedure is to charge the amine reactant, organic hydroxyl containing compound, hydrogen acceptor compound (when employed), and the selected carbonyl catalyst into the reaction vessel, introduce the proper amount of the source of carbon monoxide and then heat the mixture to obtain the desired reaction. A suitable pressure vessel, such as an autoclave, which is preferably provided with heating means and agitation means, such as a stirrer or an external rocking mechanism, is employed for the reaction.

Generally, the amount of gaseous carbon monoxide in the free space of the reactor is sufficient to maintain the desired pressure as well as to provide a reactant for the process. As the reaction progresses an additional source of carbon monoxide can be fed to the reactor either intermittently or continuously. Although greater and lesser amounts of the source of carbon monoxide can be employed if desired, generally the total amount of the source of carbon monoxide added during the reaction is between about 3 and about 50 moles and preferably between about 8 and about 15 moles of CO per group containing the active amine group of the amine reactant nitrogen atom. The highest carbon monoxide requirements are generally utilized in a process in which carbon monoxide gas is added continuously, but suitable recycle of carbon monoxide containing gas streams greatly reduces the overall consumption of carbon monoxide.

The reaction temperature is generally maintained in the range of from about 60° to about 250° and preferably from about 100° to 200° C., and more preferably from about 150° to 190° C. These temperature ranges permit a convenient rate of reaction to be achieved while avoiding undesirable side reactions. It will be understood, however, that any elevated temperatures below that at which the starting materials or the products decompose can be used. The reaction is carried out, as indicated above, at superatmospheric pressures which is normally between about 10 and about 500 atmospheres, although higher or lower reaction pressures can be employed if other reaction conditions are suitably adjusted. Preferably, however, only moderate carbon monoxide pressures in the range of about 20 to about 100 atmospheres are employed and the reaction is conveniently run at a temperature of below about 200° C. within this pressure range.

The metal carbonyl catalyst can be added to the reaction zone directly, either alone or in admixture with any other component of the reaction medium. Alternatively, the metal carbonyl catalyst can be formed in situ by adding to the reaction zone an inorganic or organic salt or complex of the metal and by employing a CO partial pressure temperature, preferably within the above cited ranges, which is sufficient to cause the carbonyl to be formed in situ. These conditions of temperature and pressure are well known. Thus, for example, dicobalt octacarbonyl can be formed in situ from an inorganic or organic cobalt salt or complex by employing in the reaction zone a CO partial pressure of at least about 3000 psi and a temperature of from about 200° to 250° C. In the event H₂ is present in the reactor (e.g., as a component of a CO gas feed stream) in a hydrogen partial pressure of at least 500 psi, the CO pressure required to form the desired metal carbonyl catalyst in situ from the added inorganic or organic salt of the metal is lowered, so that, for example, the CO partial pressure need only be at least about 2000 psi to form dicobalt octacarbonyl. The particular inorganic or organic salt which is thus charged is not critical and can comprise any salt or complex reactive with CO. Illustrative inorganic salts of the metals include the halides (Br, Cl, F, I) oxides, nitrates, carbonates, sulfides, sulfates, phosphates, and the like, and illustrative organic salts include the carboxylates (e.g., lower alkanoate salts), organo-substituted carboxylates (e.g., acetyl acetates) and the like.

The process of the present invention can be carried out batchwise, semi-continuously or even continuously.

The process of this invention can be carried out in a vapor phase or a liquid phase, or partially in vapor and liquid phases in the reaction zone.

After the reaction has been completed in the batchwise practice of this invention, the temperature of the reaction mixture can be dropped to ambient temperature and the pressure vessel vented. The reaction product is then treated by conventional procedures, including filtration, distillation, or other suitable separation techniques, to effect separation of urethane from unreacted starting material, solvent, by-product, catalyst, etc. Urea by-products, if any, can be readily recovered and recycled to the reaction zone, if desired, to suppress formation of the urea by-product therein.

In the absence of the hydrogen acceptor compounds, the process of this invention typically forms the desired urethane product in a selectivity of at least 30 mole percent, and preferably at least 40 mole percent, based on the amount of the amine reactant reacted. When such a hydrogen acceptor compound is employed in the reaction zone according to the preferred practice of the process of this invention, the desired urethane product will be generally formed in a selectivity of at least 80 mole percent, more preferably at least 90 mole percent, and most preferably at least 95 mole percent, based on the moles of the amine reactant reacted.

Thus, the amount of reaction by-products (e.g., formanilide and ureas when N-phenyl carbamates are the desired product) which are formed in the process of this invention is surprisingly low. For example, in the preferred practice of this invention using a hydrogen acceptor compound, the amount of such N-containing by-products will be formed in a selectivity of less than 20 mole percent, more preferably less than 10 mole percent, and most preferably less than 5 mole percent, based on the moles of the amine reactant reacted.

The urethane products obtained by the invention contain one or more urethane groups and can be monomeric or polymeric in nature. Thus, the process of the invention can be adapted for the preparation of monourethanes from monoamine compounds and monohydroxy compounds and adapted for the preparation of polyurethanes from polyamine compounds and monofunctional hydroxy compounds. The resulting urethane products, in particular those urethanes containing not more than three urethane groups per molecule, can be converted to corresponding isocyanates by suitable means, including thermal and catalytic means.

The process of this invention can be further illustrated by the following examples wherein parts are by weight unless otherwise indicated. In the examples, analysis of gas and liquid samples is performed by gas chromotography, with toluene being used in the liquid samples as internal standard. Urethane yields and selectivities in the examples are based on the moles of amine reactant charged and reacted, respectively, unless otherwise indicated.

EXAMPLE 1

To a 200 cc Parr reactor provided with a glass liner (actual reactor volume with liner=134 cc) and a magnetic stirrer is charged, at room temperature, 3.1 grams aniline, 15 cc methanol, and 0.29 gram of cobalt carbonyl catalyst, thereby providing a catalyst concentration of 1.9 wt. % in the charged liquid. The reactor is sealed and then purged with gaseous nitrogen by means of a gas inlet tube and, also at room temperature, CO is pressurized into the reactor, to provide a pressure in the reactor of about 1000 psig. The pressurized reactor is then heated with stirring by means of an oil bath to the 150° C. which is measured externally to the reactor. This reaction temperature is maintained for 21 hours after which the oil bath is cooled to about 30° C. by passing cooling water through a copper tube which is immersed in the bath. The gas in the reactor is then vented. Analysis of the vent gas and the liquid product mixture in the reactor shows methyl-N-phenyl carbamate is produced in a yield of about 8% and in a selectivity of about 63%, based on amine reactant charged. This represents a 157% yield of carbamate based on the amount of cobalt charged and thereby illustrates the catalytic nature of the reaction.

EXAMPLE 2

The procedure of Example 1 is repeated except that 0.17 gram of $Co_2(CO)_8$ (0.7 wt. %) is charged as the catalyst and the reaction mixture additionally contains 10 cc of 2-methoxyethyl ether as solvent. After 18 hours of reaction at 150° C., the reactor effluents are found to contain methyl-N-phenyl carbamate in a 100.5% yield, based on cobalt charged.

EXAMPLE 3

The procedure of Example 2 is repeated except that a temperature of 180° C. is used during the reaction. After 18 hours of reaction, the reactor effluents are found to contain methyl-N-phenyl carbamate in a 10% yield, based on aniline charged, which corresponds to a 335% yield based on cobalt carbonyl charged.

EXAMPLE 4

The procedure of Example 1 is repeated except that 0.31 g. of $Co_2(CO)_8$ (2.0 wt. %) is used as catalyst, without any additional solvent. After 21 hours of reaction at 180° C., the reactor effluents are found to contain methyl-N-phenyl carbamate in a 13% yield, with a 67% selectivity to the carbamate, based on aniline charged, which corresponds to a yield of 239%, based on cobalt charged.

EXAMPLES 5–16 FOR COMPARISON

To show the uniqueness of the carbonyl catalysts of this invention, the procedure of Example 1 is repeated in separate runds employing the metal compounds, solvents (if any) and reaction conditions indicated. The results thereby obtained are set forth in Table I below.

TABLE I

| Comparative Example No. | Metal Compound | (g) | (wt. %) | Solvent | (cc) | Temp. (°C.) | CO (psig) | Time (hrs.) | Methyl-N-Phenyl Carbamate % yield, on ΦNH₂ charged |
|---|---|---|---|---|---|---|---|---|---|
| 5 | RhCl . 3H₂O | 0.23 | 1.5 | — | — | 120 | 1,500 | 17 | 0 |
| 6 | 5% Pd. Alumina | 1.0 | 6.3 | — | — | 120 | 1,500 | 17 | 0 |
| 7 | [Rh(CO)ClΦ₃P]₂ | 0.69 | 4.4 | — | — | 120 | 1,000 | 18 | 0 |
| 8 | Mn₂(CO)₁₀ | 0.19 | 1.3 | — | — | 180 | 1,000 | 18 | 0 |
| 9 | Re(CO)₁₀ | 0.2 | 2.7 | dioxane | 10 | 180 | 1,000 | 12 | 0 |
| 10 | Cr(CO)₆ | 0.2 | 2.7 | dioxane | 10 | 180 | 1,000 | 12 | 0 |
| 11 | Ir(CO)₈ | 0.2 | 2.7 | dioxane | 10 | 180 | 1,000 | 12 | trace |
| 12 | V(CO)₆ | 0.2 | 2.7 | dioxane | 10 | 180 | 1,000 | 12 | 0 |
| 13 | * | 0.2 | 2.7 | dioxane | 10 | 180 | 1,000 | 12 | 0 |
| 14 | CoCl₂ | 0.2 | 2.7 | dioxane | 10 | 180 | 1,000 | 12 | trace |
| 15 | Co(O₂CCH₃)₂ | 0.2 | 2.7 | dioxane | 10 | 180 | 1,000 | 12 | trace |
| 16 | -None- | — | — | dioxane | 10 | 180 | 1,000 | 12 | 0 |

Note:
*Compound = di (cyclopentadienyl) manganese tricarbonyl.
≠Φ₃P = triphenyl phosphine.

EXAMPLE 17

The procedure of Example 1 is repeated except that the catalyst comprises 0.26 gram of Mo(CO)₆. After 18 hours of reaction at 180° C. and 1,000 psig CO pressure, methyl-N-phenyl carbamate is found to be formed in a yield of about 2% and in a selectivity of about 2%, based on aniline charged, which corresponds to a 57% yield based on molybdenum charged.

EXAMPLE 18

The procedure of Example 1 is repeated except that the catalyst comprises 0.2 gram of Fe₂(CO)₉. After 18 hours of reaction at 180° C. and 1,000 psig CO pressure, methyl-N-phenyl carbamate is found to be formed in a yield of about 2%, and in a selectivity of about 60%, based on aniline charged, which corresponds to a 50% yield based on iron charged.

EXAMPLE 19

The procedure of Example 1 is repeated except that the catalyst comprises 0.2 gram of Ni(CO)₄. After 18 hours of reaction at 180° C. and 1,000 psig CO pressure, methyl-N-phenyl carbamate is found to be formed in a yield of about 1% and in a selectivity of about 50%, based on aniline charged, which corresponds to a 20% yield based on nickel charged.

EXAMPLE 20

The procedure of Example 1 is repeated except that the catalyst comprises a titanium carbonyl complex formed by contacting 0.2 gram of biscyclopentadienyl titanium dichloride with CO at a pressure of 1,000 psig and at 180° C. for 2 hours. The carbonyl complex thus formed is then employed as catalyst as in Example 1. After 12 hours of reaction at 180° C. and 1,000 psig CO pressure, methyl-N-phenyl carbamate is found to be formed in a yield of about 9% and in a selectivity of about 90%, based on aniline charged, which corresponds to a 370% yield based on titanium charged.

EXAMPLE 21

The procedure of Example 1 is repeated except that 0.18 gram of Co₂(CO)₈ is used and except the reaction mixture also contains 10 cc of chlorobenzene as solvent. After 18 hours of reaction at 180° C., the reactor effluents are found to contain methyl-N-phenyl carbamate in a yield of about 8% and in a selectivity of about 60% based on aniline charged, which corresponds to a yield of about 253% based on the cobalt charged.

EXAMPLE 22

The procedure of Example 6 is repeated except that the solvent comprises 10 cc of p-xylene. After 18 hours of reaction at 180° C., the reactor effluents are found to contain methyl-N-phenyl carbamate in a 6% yield and 50% selectivity, based on aniline charged, which corresponds to a 190% yield based on cobalt charged.

EXAMPLE 23

The procedure of Example 1 is repeated except that 20 cc of isopropanol are used instead of the methanol of Example 1 in the charge to the reactor. After 18 hours of reaction at 180° C., the reactor effluents are found to contain isopropyl-N-phenyl carbamate in a yield of about 8% and in a selectivity of about 60%, based on aniline charged.

EXAMPLE 24 FOR COMPARISON

The procedure of Example 1 is repeated except that 0.19 g. Co₂(CO)₈ is used as catalyst and the charge to the reaction vessel includes 5.2 grams water. After 19 hours of reaction at 180° C., the reactor effluents are found to contain methyl-N-phenyl carbamate in a yield of less than 1%. This illustrates the severe adverse effect which water has on the reaction.

EXAMPLE 25

The procedure of Example 3 is repeated except that 3.5 grams ortho-toluidine are used instead of aniline, and essentially no difference in results is noted in the formation of methyl-N-ortho-tolyl carbamate.

EXAMPLE 26

The procedure of Example 3 is repeated except that 2.4 grams of N-butylamine are used instead of aniline, and essentially no difference in results is noted in the formation of methyl-N-butylcarbamate.

EXAMPLE 27

The procedure of Example 3 is repeated except that 3.3 grams of cyclohexylamine are used instead of aniline, and essentially no difference in results is noted in the formation of methyl-N-cyclo hexyl carbamate.

EXAMPLE 28

The procedure of Example 1 is repeated except that the alcohol reactant comprises, in separate runs, cyclohexanol, benzyl alcohol and butyl alcohol, respectively, and essentially no difference is noted in the formation of cyclohexyl-N-phenyl carbamate, benzyl-N-phenyl carbamate and butyl-N-phenyl carbamate, respectively.

EXAMPLE 29

The procesure of Example 3 is repeated except that 2.1 grams of 2,4-toluene diamine are employed instead of aniline. After 12 hours of reaction at 180° C. the total conversion of NH2 groups to the carbamate form is found to be 10% at a 60% selectivity to a mixture of the monocarbamate

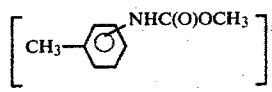

and bis-carbamate

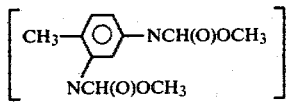

forms.

EXAMPLE 30

The procedure of Example 14 is repeated except that 3.3 grams of 4,4'-methylene dianiline is used instead of toluene diamine, and essentially no difference is noted in the formation of the mono- and bis-methyl carbamate derived from the 4,4'-methylene dianiline, e.g.,

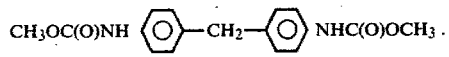

EXAMPLE 31

Following the procedure of Example 1, there is charged to the reactor in separate runs 3.1 grams aniline, 15 cc methanol, and an amount of either CoCl2, cobalt acetylacetate or cobalt naphenate sufficient to provide 1 millimole of Co. The reactor is sealed and following the N2 purge, CO is pressurized into the reactor to provide a pressure in the reactor of about 3,000 psig. After reaction at 210° C. for 18 hours in each run, analysis of the reactor effluents shows methyl-N-phenyl carbamate to be formed in each run in a yield of about 4% and in a selectivity of about 50%, based on aniline charged, which corresponds to a yield of about 130% based on cobalt charged.

EXAMPLE 32

The procedure of Example 1 is repeated except that the reaction is performed at a temperature of 120° C. for a period of 18 hours, employing a CO pressure of 1,000 psig. Analysis of the reactor effluents after this period show that methyl-N-phenyl carbamate is obtained, albeit in lower yields.

EXAMPLES 33–52

To a 200 cc Parr reactor provided with a glass liner (actual reactor volume with liner=134 cc) and a magnetic stirrer is charged, at room temperature, 3.1 grams aniline, 15 cc methanol, the desired amount of solvent (if any), the selected unsaturated organic compound, and cobalt carbonyl as catalyst. The reactor is sealed and then purged with gaseous nitrogen by means of a gas inlet tube and, also at room temperature, CO is pressurized into the reactor, to provide a pressure in the reactor of about 1000 psig. The pressured reactor is then heated with stirring by means of an oil bath to the selected temperature, which is measured externally to the reactor. This reaction temperature is maintained for the selected time after which the oil bath is cooled to about 30° C. by passing cooling water through a copper tube which is immersed in the bath. The gas in the reactor is then vented and the vent gas and the liquid product mixture in the reactor are analyzed for methyl-N-phenyl carbamate. The data thereby obtained are set forth in Table II, below.

TABLE II

| Example No. | Co2(CO)8 (g) | (wt.%) | Unsaturated Comp'd | (g) | Solvent | (cc) | Temp. (°C.) | Time (hrs) | Methyl-N-Phenyl Carbamate % Yield | % Selectivity |
|---|---|---|---|---|---|---|---|---|---|---|
| 33 | 0.17 | 0.6 | styrene | 3.6 | dioxane | 10 | 180 | 18 | 91 | 96 |
| 34 | 0.18 | 0.6 | styrene | 3.6 | dioxane | 10 | 150 | 18 | 37 | 95 |
| 35 | 0.095 | 0.3 | styrene | 3.6 | dioxane | 10 | 150 | 18 | 38 | 95 |
| 36 | 0.19 | 0.7 | styrene | 3.6 | p-xylene | 10 | 180 | 18 | 74 | >95 |
| 37 | 0.19 | 0.6 | styrene | 3.6 | chlorobenzene | 10 | 180 | 18 | 76 | 76 |
| 38 | 0.19 | 0.7 | naphthalene | 10.5 | — | — | 180 | 19 | 22 | — |
| 39 | 0.16 | 0.9 | styrene | 3.6 | — | — | 150 | 18 | 30 | — |
| 40 | 0.19 | 0.7 | styrene | 3.6 | CH3CN | 10 | 180 | 18 | 42 | 58 |
| 41 | 0.18 | 0.6 | styrene | 7.2 | dioxane | 10 | 180 | 18 | 81 | 96 |
| 42 | 0.18 | 0.6 | styrene | 3.6 | dioxane | 10 | 210 | 18 | 35 | 50 |
| 43 | 0.18 | 0.7 | styrene | 1.8 | dioxane | 10 | 180 | 18 | 51 | 74 |
| 44 | 0.18 | 0.6 | alpha-methyl styrene | 3.8 | dioxane | 10 | 180 | 18 | 73 | 96 |
| 45 | 0.18 | 0.6 | duroquinone | 4.0 | dioxane | 10 | 180 | 18 | 48 | — |
| 46 | 0.19 | 0.6 | cis-stilbene | 5.9 | dioxane | 10 | 180 | 18 | 30 | >98 |
| 47 | 0.19 | 0.6 | dimethyl indole | 4.5 | dioxane | 10 | 180 | 18 | 25 | >95 |
| 48 | 0.19 | 0.6 | cis-stilbene | 5.9 | p-xylene | 10 | 180 | 18 | 58 | >95 |
| 49 | 0.19 | 0.6 | tert-butyl anthraquinone | 8.7 | p-xylene | 10 | 180 | 18 | 41 | >95 |
| 50 | 0.19 | 0.6 | cis-stilbene | 5.9 | chlorobenzene | 10 | 180 | 48 | 70 | >95 |
| 51 | 0.19 | 0.5 | tert-butyl anthraquinone | 8.7 | chlorobenzene | 10 | 180 | 18 | 58 | >95 |
| 52 | 0.19 | 0.5 | tert-butyl anthraquinone | 8.7 | chlorobenzene | 10 | 160 | 18 | 50 | 90 |

EXAMPLE 53

The procedure of Example 39 is repeated except that 0.17 g of $Co_2(CO)_8$ is used as catalyst and the CO pressure used is 750 psig. After 18 hours of reaction at 150° C., the reactor effluents are found to contain methyl-N-phenyl carbamate in a 30% yield.

EXAMPLE 54

The procedure of Example 33 is repeated except that 0.18 g of $Co_2(CO)_8$ is used as catalyst and the CO pressure used is 500 psig. After 18 hours of reaction at 180° C., the reactor effluents are found to contain methyl-N-phenyl carbamate in a 73% yield, with 95% selectivity to the carbamate.

EXAMPLES 55–64 FOR COMPARISON

To illustrate the advantages obtained by the process of this invention, the procedure of Example 1 is repeated in separate runs employing the metal compounds, unsaturated organic compounds and reaction conditions indicated. The results thereby obtained are set forth in Table III below.

TABLE III

| Comparative Example No. | Metal Compound | (g) | (wt. %) | Unsat'd Comp'd | (g) | Solvent | (g) | Temp. (°C.) | CO (psig) | Time (hrs) | Methyl-N-Phenyl) Carbamate % Yield | % Selectivity |
|---|---|---|---|---|---|---|---|---|---|---|---|---|
| 55 | [Rh(CO)Cl$\Phi_3$P]$_2$≠ | 0.69 | 3.6 | styrene | 3.6 | dioxane | 10 | 150 | 1,000 | 18 | trace | — |
| 56 | Re(CO)$_{10}$ | 0.2 | 0.7 | styrene | 3.6 | dioxane | 10 | 180 | 1,000 | 12 | 0 | — |
| 57 | Cr(CO)$_6$ | 0.2 | 0.7 | styrene | 3.6 | dioxane | 10 | 180 | 1,000 | 12 | 0 | — |
| 58 | V(CO)$_6$ | 0.2 | 0.7 | styrene | 3.6 | dioxane | 10 | 180 | 1,000 | 12 | 0 | — |
| 59 | * | 0.2 | 0.7 | styrene | 3.6 | dioxane | 10 | 180 | 1,000 | 12 | 0 | — |
| 60 | CoCl$_2$ | 0.2 | 0.7 | styrene | 3.6 | dioxane | 10 | 180 | 1,000 | 12 | trace | — |
| 61 | Co(O$_2$CCH$_3$)$_2$ | 0.2 | 0.7 | styrene | 3.6 | dioxane | 10 | 180 | 1,000 | 12 | trace | — |
| 62 | Co$_2$(CO)$_8$ | 0.18 | 0.6 | p-benzoquinone | 3.6 | dioxane | 10 | 180 | 1,000 | 18 | trace | — |
| 63 | Co$_2$(CO)$_8$ | 0.18 | 0.6 | naphthoquinone | 5.2 | dioxane | 10 | 180 | 1,000 | 18 | trace | — |
| 64 | Co$_2$(CO)$_8$ | 0.18 | 0.5 | chloranil | 8.0 | dioxane | 10 | 180 | 1,000 | 18 | trace | — |

*compound = cyclopentadienyl manganese tricarbonyl.
′ $\Phi_3$P = triphenyl phosphine.

Examples 62 through 64 show that not all unsaturated compounds are useful as hydrogen acceptors in the practice of this invention. Thus, as seen from Examples 62 and 63, unsubstituted benzoquinone and naphthoquinone under the conditions of reaction there reported produce only trace amounts of the desired carbamate product. Likewise, chloranil, which is a tetrachloro-substituted para-quinone, also produces, under the conditions of Example 64, only trace carbamate. Similarly, if the procedure of Example 33 is repeated employing hexene-1 instead of styrene, carbamate is obtained in a yield of less than about 10% under the conditions of such an experiment, and carbonylated by-products of hexene-1 are observed.

EXAMPLE 65

The procedure of Example 46 is repeated except that 20 cc of isopropanol are used instead of the methanol of Example 46 in the charge to the reactor. After 18 hours of reaction at 180° C., the reactor effluents are found to contain isopropyl-N-phenyl carbamate in a yield of about 31% and in a selectivity of greater than about 95%.

EXAMPLE 66 FOR COMPARISON

The procedure of Example 33 is repeated except that 0.19 g $Co_2(CO)_8$ is used as catalyst and the charge to the reaction vessel includes 5.2 grams water. After 19 hours of reaction at 180° C., the reactor effluents are found to contain methyl-N-phenyl carbamate in a yield of less than 5%. This illustrates the severe adverse effect which water has on the reaction in the presence of the hydrogen acceptor compounds of this invention.

EXAMPLE 67

The procedure of Example 33 is repeated except that 0.18 gram of $Fe_2(CO)_9$ is used as catalyst. After 18 hours of reaction at 180° C. using 1000 psig CO pressure, the reactor effluents are found to contain methyl-N-phenyl carbamate in a yield of about 4% and in a selectivity of about 85%, which represents a yield of about 185% based on iron charged. This is an approximate 2-fold improvement in a yield of carbamate obtained in the absence of styrene, as can be seen by comparison with Example 18.

EXAMPLE 68

The procedure of Example 33 is repeated except that 0.2 gram of $Ni(CO)_4$ is used as catalyst. After 12 hours of reaction at 180° C. employing a CO pressure of 1000 psig, the methyl-N-phenyl carbamate is found to be formed in a yield of about 3% and in a selectivity of about 85%. Again, this represents about a 300% improvement in a yield over that amount obtained in the absence of the sytrene, as is seen by comparison with the results of Example 19.

EXAMPLE 69

The procedure of Example 33 is repeated except that 0.2 gram of $Ir_2(CO)_8$ is used as catalyst. After 12 hours of reaction at 180° C. employing a CO pressure of 1000 psig, methyl-N-phenyl carbamate is found to be present in a yield of about 2.5% and a selectivity of about 85%, which represents a yield of about 250% based on iridium charged.

EXAMPLE 70

The procedure of Example 33 is repeated except that the catalyst comprises 0.2 gram of the titanium carbonyl complex prepared as in Example 20. After 12 hours of reaction at 180° C., the reactor effluents are found to contain methyl-N-phenyl carbamate in a yield of about 9% and in a 370% selectivity. The carbamate yield thereby obtained is a 370% improvement over that yield of product obtained in Example 20 in the absence of styrene.

EXAMPLE 71

The procedure of Example 36 is repeated except that 3.5 grams ortho-toluidine are used instead of aniline, and essentially no difference in results is noted in the formation of methyl-N-ortho-tolyl carbamate.

EXAMPLE 72

The procedure of Example 36 is repeated except that 2.4 grams of N-butylamine are used instead of aniline, and essentially no difference in results is noted in the formation of methyl-N-butylcarbamate.

EXAMPLE 73

The procedure of Example 36 is repeated except that 3.3 grams of cyclohexylamine are used instead of aniline, and essentially no difference in results is noted in the formation of methyl-N-cyclo hexyl carbamate.

EXAMPLE 74

The procedure of Example 33 is repeated except that the alcohol reactant comprises, in separate runs, cyclohexanol, benzyl alcohol and butyl alcohol, respectively, and essentially no difference is noted in the formation of cyclohexyl-N-phenyl carbamate, benzyl-N-phenyl carbamate and butyl-N-phenyl carbamate, respectively.

EXAMPLE 75

The procedure of Example 37 is repeated except that 2.1 grams of 2,4-toluene diamine are employed instead of aniline. After six hours of reaction at 180° C. the total conversion of $NH_2$ groups to the carbamate form is found to be 75% at a selectivity to the monocarbamate

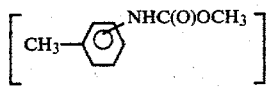

of about 30% and at a selectivity to the bis-carbamate form

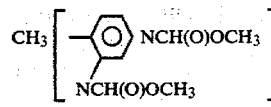

of about 30%.

EXAMPLE 76

The procedure of Example 75 is repeated except that 3.3 grams of 4,4'-methylene dianiline is used instead of toluene diamine, and essentially no difference is noted in the formation of the mono- and bis-methyl carbamate derived from the 4,4'-methylene dianiline, e.g.,

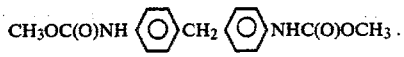

EXAMPLE 77

Example 36 is repeated except that 0.18 gram of cobalt carbonyl is employed as catalyst and 3.8 grams of 2,3-dimethyl butene-2 is employed instead of styrene. After 18 hours of reaction at a temperature of 180° C. and a CO pressure of 1,000 psig, the reactor effluents are found to contain methyl-N-phenyl carbamate in a yield of about 14.2%, with a selectivity of greater than 90% to the carbamate.

EXAMPLE 78

The procedure of Example 34 is repeated except that 5.3 grams of isobutylene are employed instead of styrene. After 18 hours of reaction at a temperature of 150° C. and a CO pressure of 1,000 psig, the reactor effluents are found to contain methyl-N-phenyl carbamate in a yield of about 12% with a selectivity of about 90% to the carbamate.

EXAMPLE 79

The procedure of Example 1 is repeated except that 0.45 gram of $[Rh(CO)Cl]_2$ is used as catalyst. After 22 hours of reaction at a temperature of 150° C. employing a CO pressure of 1,000 psig, the reactor effluent is found to contain methyl-N-phenyl carbamate in a yield of about 0.5% and in a selectivity of about 50%, based on the aniline charged.

EXAMPLE 80

The procedure of Example 79 is repeated except that the charge to the reactor additionally contains 10 cc of dioxane and 3.6 grams of styrene. After 18 hours of reaction at a temperature of 150° C. and a CO pressure of 1,000 psig, the reactor effluents are found to contain methyl-N-phenyl carbamate in a yield of about 1.8% and in a selectivity of about 80%, based on the aniline charged. This represents an increase of about 260% in the yield of carbamate over the results achieved without styrene in Example 79.

In comparison with the advantageous results achieved in Examples 79 and 80, it can be seen that Examples 7 and 55 above illustrate the adverse effect on product yield when a triaryl phosphine is employed in combination with a metal carbonyl catalyst of this invention.

EXAMPLE 81

Following the procedure of Example 1, 15 cc of methanol, 3.1 grams of aniline, and 10 cc of dioxane, together with 0.18 gram of $Co_2(CO)_8$ as catalyst is charged to the reactor in a first run. After purging the reactor with nitrogen, CO is pressurized into the reactor to provide 1000 psig of CO. The reaction is carried out at a temperature of 180° C. for a period of 19 hours. After this time, the reactor effluents are analyzed and methyl-N-phenyl carbamate is found to be formed in a yield of about 335%, based on cobalt charged.

In a separate run, the foregoing procedure is repeated except that the charge to the reactor additionally contains 4.0 grams of nitrobenzene. After 19 hours of reaction at a temperature of 180° C. and a CO pressure of 1000 psig, analysis of the reactor effluent from this second run shows methyl-N-phenyl carbamate to be formed in a yield of only 100%, based on cobalt charged, with a selectivity to a carbamate of only 50%, based on cobalt charged. The balance of products is found to comprise predominantly formanilide, with a minor quantity of diphenyl urea also being formed. There is also observed to be formed during the reaction a precipitate comprising $Co(OH)_2$, resulting from the reaction of cobalt with water which is formed in the reaction mixture from $-NO_2$ moieties in the system. The water therefore adversely combines with the cobalt carbonyl and removes the desired catalyst from the reaction.

EXAMPLE 82

The procedure of Example 81 is repeated except that the reaction mixture in each run also contains 3.6 grams of styrene. After 19 hours of reaction at 180° C. and 1000 psig CO pressure, the reactor effluents in the first run are found to contain methyl-N-phenyl carbamate in a yield of about 80% and in a 95% selectivity. In the second run wherein the nitrobenzene is also charged, the methyl-N-phenyl carbamate yield is found to be only 3%, and a Co(OH)₂ precipitate is also observed to be formed in substantial amounts.

Examples 81 and 82 illustrate the adverse effect of nitrogeneous moieties (e.g., —NO₂ and —NO) on carbamate formation using the carbonyl catalysts of this invention. The process of this invention, therefore, is preferably conducted in the substantial absence of such nitrogeneous moieties.

Analysis of the product mixtures obtained following the reactions according to the process of this invention in Examples 1-4, 17-23, 25-54, 65, 70-80, 81 (Run 1) and 82 (Run 1) above show no detectable concentration of any such nitrogeneous moiety, using an analytical technique sensitive to a level of 0.01 weight percent.

It will be obvious that various changes and modifications can be made without departing from the invention, and it is intended, therefore, that all matter contained in the foregoing description shall be interpreted as illustrative only and not as limitative of the invention.

I claim:

1. A process for producing urethanes which comprises contacting a reactant consisting essentially of an organic primary or secondary amine selected from the group consisting of aliphatic amines, alicyclic amines and aromatic amines having the formula
   (i) RNH₂,
   (ii) RNH(R'), or
   (iii) R(NH₂)ₘ
wherein R and R' are independently selected from a group consisting of alkyl, aryl, alkaryl, aralkyl, and cycloalkyl and wherein m is an integer of from 2 to 5, and substituted derivatives of the above groups wherein the substituent is inert and is alkyl, aryl, alkaryl, aralkyl, cycloalkyl, halogen, alkylcyano, tertiary amino, ether or thioether, and amino-substituted derivatives of the foregoing hydrocarbyl substituents, said amine being free of substitution by OH—, >C=O and sulfonic acid groups, in a reaction zone in the substantial absence of reactive oxygen and in the substantial absence of —NO and —NO₂ moieties, under substantially anhydrous conditions, and at elevated temperature and pressure, with (1) a source of carbon monoxide and (2) an organic compound containing at least one hydroxyl group and consisting essentially of at least one member selected from the group consisting of compounds of the formula Z(OH)ₙ wherein n is an integer of at least one and Z is an optionally substituted aliphatic, cycloaliphatic or araliphatic group, in the presence of (3) an effective amount of catalyst consisting essentially of a member selected from the group consisting of carbonyls of a metal selected from the group consisting of Co, Mo, Ti, Ni, Fe, Rh and mixtures thereof, said catalyst calculated as the metal, being present in an amount of at least about 0.001 weight percent of the amine reactant charged to the reaction zone.

2. The process according to claim 1, wherein the amine comprises at least one member of the group consisting of primary amines of up to 24 carbon atoms.

3. The process according to claim 1, wherein the amine comprises at least one member selected from the group consisting of aromatic primary amines of from 6 to 24 carbon atoms.

4. The process according to claim 1, wherein the amine comprises at least one member selected from the group consisting of aniline and alkyl-substituted anilines of up to 12 carbon atoms.

5. The process according to claim 1, wherein the hydroxyl group-containing compound consists essentially of at least one member selected from the group consisting of monohydric alcohols having from 1 to 20 carbon atoms.

6. The process according to claim 1, wherein the hydroxyl group-containing compound consists essentially of at least one member selected from the group consisting of polyhydric compounds containing up to 20 carbon atoms.

7. The process according to claim 1, wherein the hydroxyl group-containing compound consists essentially of a lower alkanol having from 1 to 10 carbon atoms.

8. The process according to claim 1, wherein the amine is contacted with said compounds, carbon monoxide and catalyst at a temperature of from about 130° C. to 250° C.

9. The process according to claim 1, wherein said amine comprises an aromatic primary mono- or di-amine of from 6 to 14 carbon atoms, said hydroxyl group-containing compound comprises a mono- or poly-hydric alcohol of up to 7 carbon atoms, and said reaction is conducted at a temperature of from about 100° to 200°.

10. The process according to claim 9, wherein the catalyst consists essentially of cobalt carbonyl.

11. The process according to claim 1 wherein said reaction zone additionally contains at least one unsaturated organic compound having at least four carbon atoms per molecule and containing one or more non-aryl C=C or C=N bonds per molecule, with the proviso that each terminal non-aryl >C=CH₂ group which is not aryl-substituted in said unsaturated compound must contain hydrocarbyl di-substitution on the β-carbon atom of each such terminal >C=CH₂ group, and with the further proviso that the ring carbon atoms in any quinone-moiety in said unsaturated compound are hydrocarbyl substituted, said unsaturated organic compound being employed in at least an equimolar amount with said amine.

12. The process according to claim 11, wherein said unsaturated organic compound comprises at least one member from the group consisting of aralkenes; cycloalkenes; alkyl esters of unsaturated carboxylic acids; cycloaliphatic dienes; polynuclear aromatic compounds containing two or more aromatic rings per molecule; indole; alkenes having the formula (I):

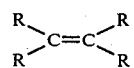

wherein the R groups are the same or different and are H or hydrocarbyl of from 1 to 10 carbon atoms, with the proviso that at least two R groups are hydrocarbyl; quinones of the formula (II):

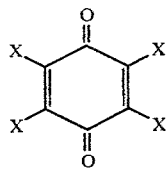
(II)

and of the formula (III):

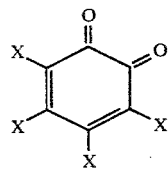
(III)

wherein the X groups are the same or different and are hydrocarbyl of from 1 to 10 carbon atoms; napthaquinones of the formula (IV):

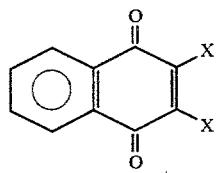
(IV)

and of the formula (V):

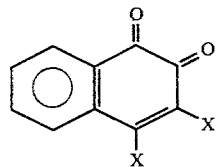
(V)

and of the formula (VI):

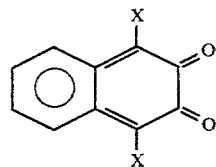
(VI)

wherein the X groups are of the same or different and are as defined above; Shiff bases of the formula (VII), (VIII) or (IX)

$$X_2C=NX \quad (VII)$$

$$X-N=C-X-C=N-X \quad (VIII)$$

$$X-C=N-X-N=C-X \quad (IX)$$

wherein the X groups are the same or different and are as defined above; aliphatic dienes wherein any terminal >C=CH$_2$ groups are β-hydrocarbyl substituted; derivatives of the foregoing in which one or more ring carbon atom in non-quinonyl aryl groups is replaced by an oxygen, sulfur or nitrogen atom; and derivatives of the foregoing in which non-quinonyl aryl groups are substituted by one or more members selected from the group consisting of hydrocarbyl group of from 1 to 10 carbon atoms, halo and halo-substituted hydrocarbyl of 1 to 10 carbon atoms.

13. The process according to claim 11, wherein said unsaturated organic compound is employed in a unsaturated organic compound: amine reactant molar ratio of from at least 1:1 to about 4:1.

14. A process for producing urethanes which comprises contacting a reactant consisting essentially of an organic primary or secondary amine selected from the group consisting of aliphatic amines, alicyclic amines and aromatic amines having the formula (i) RNH$_2$,
(ii) RNH(R'), or
(iii) R(NH$_2$)$_m$ wherein R and R' are independently selected from the group consisting of alkyl, aryl, alkaryl, aralkyl, and cycloalkyl and wherein m is an integer of from 2 to 5, and substituted derivatives of the above groups wherein the substituent is inert and is alkyl, aryl, alkaryl, aralkyl, cycloalkyl, halogen, alkylcyano, tertiary amino, ether or thioether, and amino-substituted derivatives of the foregoing hydrocarbyl substituents, said amine being free of substitution by OH—, >C=O and sulfonic acid groups, in a reaction zone in the substantial absence of reactive oxygen and in the substantial absence of —NO and —NO$_2$ moieties, under substantially anhydrous conditions, and at elevated temperature and pressure, with (1) a source of carbon monoxide, (2) an organic compound containing at least one hydroxyl group and consisting essentially of at least one member selected from the group consisting of compounds of the formula Z(OH)$_n$ wherein n is an integer of at least one and Z is an optionally substituted aliphatic, cycloaliphatic or araliphatic group, and (3) at least one unsaturated organic compound having at least four carbon atoms per molecule and containing one or more non-aryl C=C or C=N bonds per molecule, with the proviso that each terminal non-aryl >C=CH$_2$ group which is not aryl-substituted in said unsaturated compound must contain hydrocarbyl disubstitution on the β-carbon atom of each such terminal >C=CH$_2$ group, and with the further proviso that the ring carbon atoms in any quinone-moiety in said unsaturated compound are hydrocarbyl substituted, said unsaturated organic compound being employed in an amount sufficient to provide a mole ratio of the unsaturated organic compound to amine reactant of at least about 1:1, said amine reactant, carbon monoxide source, hydroxyl-containing compound and unsaturated compound being contacted in the presence of iridium carbonyl as catalyst, said catalyst, calculated as the metal, being present in an amount of at least about 0.001 weight percent of the amine reactant charged to the reaction zone.

15. The process according to claim 11 wherein the unsaturated organic compound comprises a member selected from the group consisting of styrene, alpha-methyl styrene, stilbene, tert-butyl anthaquinone, ethyl-anthra-quinone, tetramethyl parabenzoquinone, tetraethyl parabenzoquinone and duroquinone.

* * * * *

UNITED STATES PATENT AND TRADEMARK OFFICE
CERTIFICATE OF CORRECTION

PATENT NO. : 4,266,070
DATED : May 5, 1981
INVENTOR(S) : David Moy

It is certified that error appears in the above—identified patent and that said Letters Patent are hereby corrected as shown below:

Col. 1, line 10 - "May 9, 1979" should be --May 25, 1979--
Col. 1, line 11 - delete "filed on even date herewith"
Col. 3, line 52 - "teritary" should be --tertiary--
Col. 5, line 3 - "stiochiomet-" should be --stoichiomet- --
Col. 6, line 25 - "Z" should be --Z'--
Col. 7, line 24 - "lauryl alochol" should be --lauryl alcohol--
Col. 9, line 49 - "napthaqui-" should be --naphthaqui- --
Col. 10, line 37 - delete one "aryl,"
Col. 10, line 67 - "methacralate" should be --methacrylate--
Col. 14, line 3 - "chromotography" should be --chromatography--
Col. 14, line 65 - "runds" should be --runs--
Col. 15, Table I - add "$\neq$" superscript to the formula in the "Metal Compound" column for Comparative Example No. 7
Col. 17, line 5 - "procesure" should be --procedure--
Col. 17, line 42- "naphenate" should be --naphthenate--
Col. 18, Table II - In Example 46, "$>$98" should be -- $>$96--
Col. 25, line 21 - "napthaqui-" should be --naphthaqui- --

Signed and Sealed this

Thirtieth Day of March 1982

[SEAL]

Attest:

GERALD J. MOSSINGHOFF

Attesting Officer   Commissioner of Patents and Trademarks